Figures 1, 2:
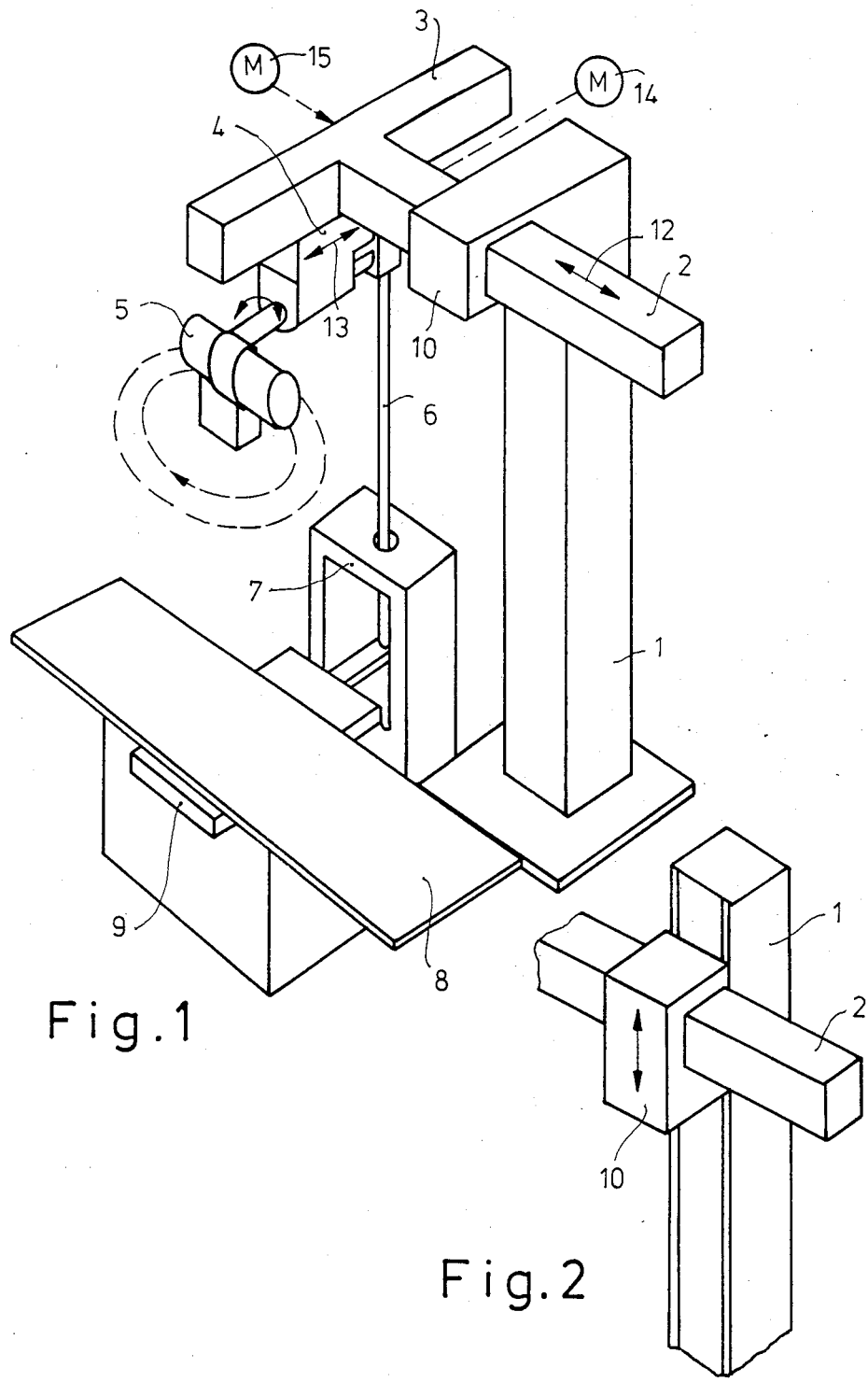

United States Patent [19]

Hepke

[11] Patent Number: 4,628,524
[45] Date of Patent: Dec. 9, 1986

[54] X-RAY TOMOGRAPH

[75] Inventor: Jürgen Hepke, Hamburg, Fed. Rep. of Germany

[73] Assignee: U.S. Philips Corporation, New York, N.Y.

[21] Appl. No.: 703,636

[22] Filed: Feb. 21, 1985

[30] Foreign Application Priority Data

Feb. 24, 1984 [DE] Fed. Rep. of Germany ....... 3406717

[51] Int. Cl.⁴ .............................................. H05G 1/02
[52] U.S. Cl. ...................................... 378/197; 378/25
[58] Field of Search ....................... 378/197, 27, 25, 21, 378/24, 196, 193, 11; 248/DIG. 13

[56] References Cited

U.S. PATENT DOCUMENTS 2,491,224 12/1949 Stava .................................... 378/196
3,655,967 4/1972 Finkenzeller et al. ............... 378/196
3,714,427 1/1973 Reiniger et al. ....................... 378/25

FOREIGN PATENT DOCUMENTS 1250594 6/1962 Fed. Rep. of Germany ...... 378/197

Primary Examiner—Craig E. Church
Assistant Examiner—Charles F. Wieland
Attorney, Agent, or Firm—Jack E. Haken

[57] ABSTRACT

The invention relates to an X-ray tomograph in which the X-ray tube can perform movements which are independent of each other in two directions at right angles to each other. The X-ray tube in a first support can be moved in the transverse direction which is connected to a second support extending in the longitudinal direction which in its main direction is journalled so as to be movable in a stand connected to the floor.

3 Claims, 2 Drawing Figures

X-RAY TOMOGRAPH

The invention relates to an X-ray tomograph having an X-ray tube which is movable in a horizontal plane in the longitudinal direction and independently thereof in the transverse direction of an examination table and which is coupled to a picture recording unit via a control rod.

Such a tomograph is known from German OS No. 19 36 915. As a result of the movability of the X-ray tube in the longitudinal direction and independently thereof in the transverse direction such an apparatus enables the performance of any blurring patterns situated in a horizontal plane. The X-ray tube in the known device is connected to a telescope-like ceiling suspension unit which is supported by a first carriage which can be moved in rails extending in the transverse direction and which are connected to a second carriage which can be moved in rails extending in the longitudinal direction. These latter rails are connected to the ceiling. For such an apparatus a sufficiently stable ceiling construction is required and measures must be taken to prevent vibrations from adversely influencing the picture quality during a tomographic record.

Furthermore, a tomograph is known from German PS No. 12 50 594 in which the X-ray tube is connected to a support which can be moved in a guide in the transverse direction. The guide is slidable in the longitudinal direction of a vertical column which in turn can be moved on rails on the floor and at the ceiling in the longitudinal direction. The movements in the longitudinal and transverse directions are mechanically coupled together so that only certain blurring patterns are possible. In this case also the set-up is possible only by means of a ceiling construction also when the supportability thereof may be smaller than in the preceding case. However, for that case a floor rail is necessary.

It is the object of the invention to construct an X-ray apparatus in such manner that neither a ceiling construction nor a floor rail is required.

According to the invention this is achieved in that the X-ray tube in a first support can be moved in the transverse direction, that the first support is connected to the end of a second support which extends in the longitudinal direction and is journalled in said direction so as to be movable in a stand which can be connected to the floor.

The invention will now be described in greater detail with reference to the drawing in which FIG. 1 shows a first embodiment and FIG. 2 shows a part of a second embodiment.

Reference numeral 1 in FIG. 1 denotes a stationary stand in the form of a vertical column which is connected to the floor and which at its upper end comprises a angular guide 10 in which a support 2 is journalled so as to be movable horizontally and in the direction of the arrow 12, i.e. in the longitudinal direction of the table. At one end of the support 2 extending in the longitudinal direction of the table a support 3 is connected so as to extend at right angles thereto in such manner that the two supports 2 and 3 form a T which is situated in a horizontal plane. A carriage 4 is guided in the support 3 in the longitudinal direction thereof, i.e. in the direction of the arrow 13, so as to be movable and supports an X-ray tube 5 and is coupled to one end of a coupling rod 6 which is journalled universally in a bearing not further shown in the stand 7 and whose other end is connected to a cassette drawer comprising a film cassette. The cassette drawer is present below the examination table 8 on which a patient is positioned during the examination. The longitudinal direction of the examination table corresponds to the arrow 12 and the transverse direction corresponds to the arrow 13.

The movement of the carriage 4 inside the support 3 in the transverse direction and the movement of the carrier 2 inside the guide 10 in the longitudinal direction is effected by means of the diagrammatically shown motors 14 and 15. When the speed variations thereof are matched to each other in a suitable manner as a function of time the X-ray tube and the film drawer 9, respectively, coupled mechanically thereto by means of the control rod 6 can perform any blurring patterns. The motor 14 for the transverse movement may be provided in the carriage 4 and, in a manner not shown, may drive a nut which travels on a screw spindle so that the carriage upon rotating the spindle is moved in the direction of the arrow 13. This type of drive is known inter alia from German AS No. 19 36 915. In a similar manner the support 2 is moved by means of the motor 15 provided in the guide 10 and acting on a nut which cooperates with a spindle connected to the support 2.

In contrast with the known apparatus according to German AS No. 19 36 915, a direct coupling exists between the X-ray tube and the cassette drawer, which is in favour of the picture quality. A ceiling construction is not required and in spite of a smaller construction at least the same stability is obtained. The apparatus is readily accessible from all sides, because floor rails and the like are absent.

The FIG. 2 embodiment differs from that of FIG. 1 in that the guide 10 in which the support 2 is journalled is not rigidly connected to the column 1 but is connected thereto so as to be vertically movable—similar to the tomograph according to German PS No. 12 50 594. As a result of this it is possible for an X-ray tomographic record to adapt the height of the horizontal plane in which the X-ray tube 5 is moved to the relevant requirements. The adjustability of the X-ray tube in height is also of interest for records other than tomographic records, for example, records on wall suspended stands or records with larger SID on the table.

What is claimed is:

1. An X-ray tomograph comprising:
    X-ray table means for horizontally supporting a patient undergoing examination above a floor;
    X-ray picture recording means disposed beneath the table means;
    a vertical support column having a first end which is rigidly attached to the floor near the table means and a second end which extends from the floor above the height of the table means;
    angular guide means attached to the second end of the column;
    first horizontal support means journalled in said guide means for horizontal motion parallel to a longitudinal direction of the table means;
    second horizontal support means affixed to one end of the first horizontal support means;
    carriage means journalled in the second support means for horizontal motion perpendicular to the longitudinal direction of the table means;
    an X-ray tube connected to the carriage means for projecting X-rays through the table means to the recording means;

a coupling rod connecting the carriage means to the recording means to produce coordinated motion of the carriage means and the recording means; and motor means for horizontally displacing the first support parallel to the longitudinal direction with respect to the guide means and for horizontally displacing the carriage, perpendicular to the longitudinal direction, with respect to the second support means.

2. The apparatus of claim 1 wherein the center of the second support means is affixed to one end of the first support means to form a T-shaped structure.

3. The apparatus of claim 1 or 2 wherein the guide means is vertically displaceable with respect to the column.

* * * * *